(12) United States Patent
Kush et al.

(10) Patent No.: US 9,020,878 B2
(45) Date of Patent: Apr. 28, 2015

(54) INTELLIGENT AIRFOIL COMPONENT SURFACE INSPECTION

(75) Inventors: Matthew T. Kush, Martinsville, IN (US); Kong Ma, Carmel, IN (US); Robert Moriarty, Greenwood, IN (US)

(73) Assignee: Rolls-Royce Corporation, Indianapolis, IN (US)

( * ) Notice: Subject to any disclaimer, the term of this patent is extended or adjusted under 35 U.S.C. 154(b) by 518 days.

(21) Appl. No.: 13/416,409

(22) Filed: Mar. 9, 2012

(65) Prior Publication Data

US 2012/0233111 A1  Sep. 13, 2012

Related U.S. Application Data

(60) Provisional application No. 61/451,036, filed on Mar. 9, 2011.

(51) Int. Cl.
*G06K 9/00* (2006.01)
*G01N 21/91* (2006.01)

(52) U.S. Cl.
CPC ..................... *G01N 21/91* (2013.01)

(58) Field of Classification Search
CPC .............................. G06N 5/048; G01N 21/41
USPC ........................................................... 706/12
See application file for complete search history.

(56) References Cited

U.S. PATENT DOCUMENTS

| | | | |
|---|---|---|---|
| 4,968,892 A | 11/1990 | McAtee | |
| 5,544,256 A | 8/1996 | Brecher et al. | |
| 6,091,846 A | 7/2000 | Lin et al. | |
| 6,397,122 B1 | 5/2002 | Lindstrom et al. | |
| 6,542,249 B1 | 4/2003 | Kofman et al. | |
| 7,397,550 B2 | 7/2008 | Hackney et al. | |
| 2004/0139039 A1 | 7/2004 | Mon | |
| 2005/0220335 A1 | 10/2005 | Budd | |

OTHER PUBLICATIONS

International Search Report and Written Opinion, ISA/US, PCT/US2012/028477, Rolls-Royce Corporation, Jul. 5, 2012.
International Search Report and Written Opinion, ISA/US, PCT/US2012/028636, Rolls-Royce Corporation, Aug. 16, 2012.

*Primary Examiner* — David Vincent
*Assistant Examiner* — Ola Olude Afolabi
(74) *Attorney, Agent, or Firm* — Shumaker & Sieffert, P.A./Rolls-Royce Corporation

(57) ABSTRACT

An apparatus includes a positioning system; a surface indicator system to collect an indication data set from a surface of a component utilizing a fluorescent penetration process; an indication data processing system to create an output data set in response to the indication data set utilizing a fuzzy logic algorithm; and a microprocessor to provide at least one surface variance in response to the indication data set and the output data set. A method including conducting a surface indication technique for a component; utilizing a positioning algorithm to manipulate positioning equipment in response to the component; directing an indication source to a surface of the component; collecting an indication data set in response to directing the indication source; applying a fuzzy logic analysis in response to the indication data set to provide an output data set; and providing at least one surface variance in response to the output data set.

20 Claims, 3 Drawing Sheets

INTELLIGENT AIRFOIL COMPONENT SURFACE INSPECTION

CROSS REFERENCE TO RELATED APPLICATIONS

The present application claims the benefit of U.S. Provisional Patent Application 61/451,036, filed Mar. 9, 2011, and is incorporated herein by reference. This application also incorporates by reference, in their entirety, the following concurrently filed applications: INTELLIGENT AIRFOIL COMPONENT SURFACE IMAGING INSPECTION, Ser. No. 13/416,315; INTELLIGENT AIRFOIL COMPONENT GRAIN DEFECT INSPECTION, Ser. No. 13/416,516; AUTOMATED OBJECT MANIPULATION SYSTEM, Ser. No. 13/416,705; PROTOCOL-BASED INSPECTION SYSTEM, Ser. No. 13/416,610; and ILLUMINATION SYSTEM WITH ILLUMINATION SHIELD, Ser. No. 13/416,770.

TECHNICAL FIELD

The present invention generally relates to surface inspection processes, and more particularly, but not exclusively, to an automated surface inspection process including fuzzy logic analysis.

BACKGROUND

Present approaches to surface inspection processes suffer from a variety of drawbacks, limitations, disadvantages and problems including those respecting efficiency, repeatability and others. There is a need for the unique and inventive automated surface inspection apparatuses, systems and methods disclosed herein.

SUMMARY

One embodiment of the present invention is a unique automated surface inspection process. Other embodiments include apparatuses, systems, devices, hardware, methods, and combinations for an automated surface inspection process including fuzzy logic analysis. Further embodiments, forms, features, aspects, benefits, and advantages of the present application shall become apparent from the description and figures provided herewith.

DETAILED DESCRIPTION OF THE ILLUSTRATIVE EMBODIMENTS

Figure 1:
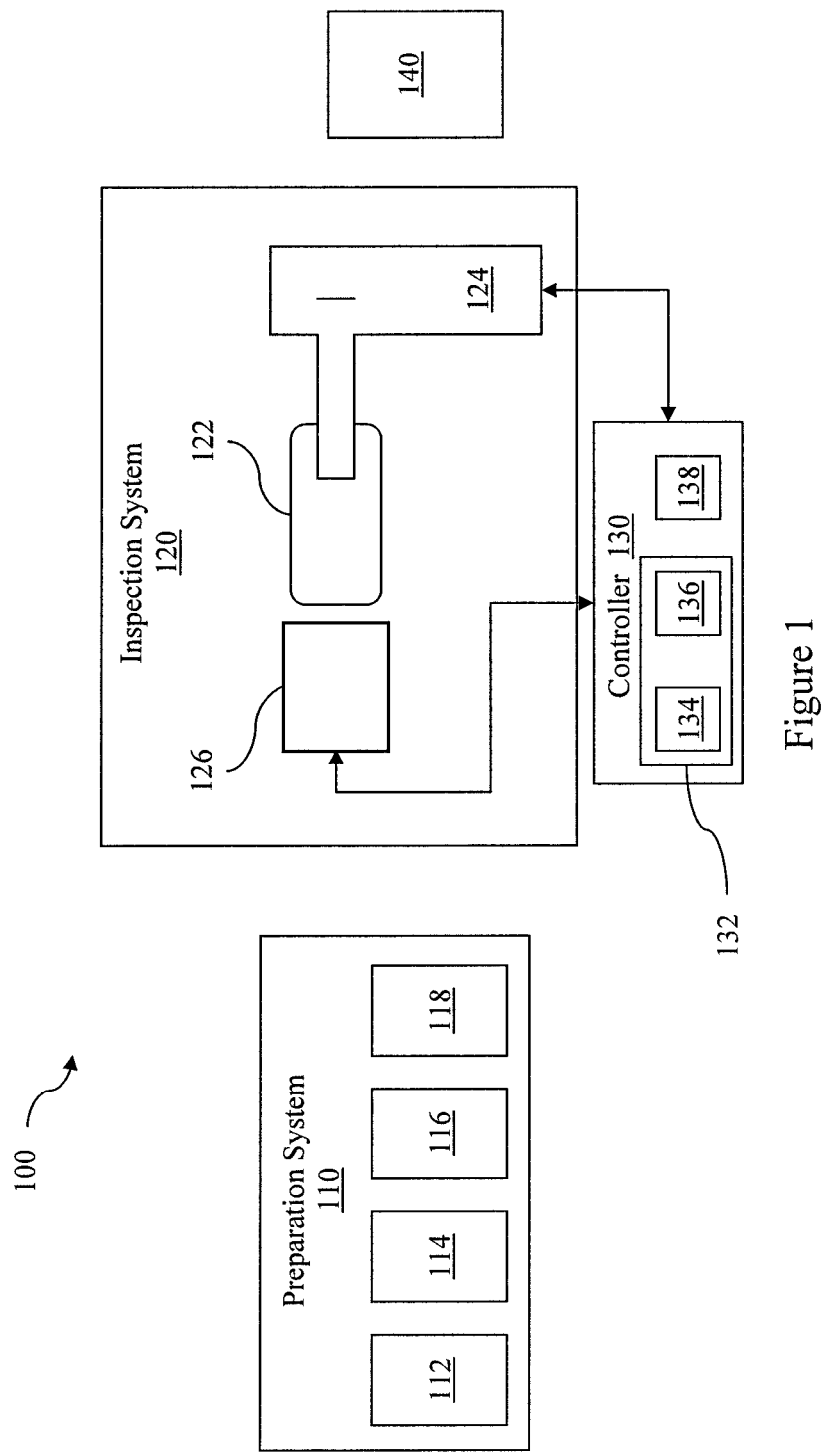
FIG. 1 is an illustration of one embodiment of a surface inspection system.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

One embodiment of a surface inspection system from the present application includes applying a surface inspection technique such as but not limited to liquid penetrant and magnetic-particle inspection, applying a positioning algorithm to efficiently manipulate a sensor and a component with robotic positioning and applying fuzzy logic analysis to identify surface anomalies of the component indicated by the surface inspection system.

With reference to FIG. 1, an illustration is shown for a surface inspection system 100 representing a non-limiting embodiment of the present invention including an automated surface inspection process, algorithms, sensors, robotic positioning, and analysis to locate, evaluate and report surface variances. Surface inspection system 100 is shown to include a preparation system 110, an inspection system 120 and a controller 130.

Preparation system 110, as shown in this embodiment, has four stages. In other embodiments, each stage can have multiple levels and one stage can be combined with another stage. In yet other embodiments, one or more of the stages may not be included. The embodiment shown with preparation system 110 includes an initial cleaning process 112, an indicator application process 114, an excess indicator removal process 116, and a developer application process 118.

Initial cleaning process 112 can be included when the surface of a part 122 contains contamination such as but not limited to lubricant and material shavings from previous manufacturing processes or other sources. A surface of a part that is clear of oil or debris can reduce the opportunity for obscuring an anomaly or falsely indicating a defect on the surface. Indicator application process 114 can include application techniques available to an operator including but not limited to dipping, brushing and spraying. Indicators can include liquid indicators such as a dye or non-liquid indicators such as magnetic-particles.

Application parameters for indicator application process 114 can depend on the indicator chosen and the types of anomalies anticipated. For example, dyes with lower viscosity may penetrate faster and small anomalies may require more time for penetration. In some applications, surface porosity may affect the ability of a liquid indicator to adequately indicate surface defects and adjustments can be made to the application parameters.

Excess indicator removal process 116 can remove substantially all of the excess indicator from a surface without removing too much indicator which can affect the accuracy of an surface inspection test. Not removing enough of the excess indicator can lead to false indications and removing more than just the excess indicator can deplete the amount of indicator necessary on the surface for indicating anomalies. In developer application process 118, a developer can be used in some embodiments which apply certain types of indicators to provide additional contrast between a fluorescent dye and the surrounding surfaces.

Once part 122 has been prepared with preparation system 110, an embodiment of surface inspection system 100 can continue with inspection system 120. Inspection system 120, as shown in the embodiment of FIG. 1, includes a positioning system 124 and an indication system 126.

Positioning system 124 of this embodiment operates with a part presentation technique based on an algorithm for manipulating part 122 in an efficient manner with minimum hunting for part surfaces and anomalies. Embodiments of positioning system 124 can include a robotic part manipulator with a discussion of further details to follow. In one particular embodiment, positioning system 124 utilizes illumination and imaging components to identify the type of part 122 being inspected. Illumination can be, for example, supplied for reflection detection or shadow detection. An imaging component can be, for example, a camera capable of reproducing the image, a photo sensor capable of detecting illumination, or the like.

Positioning system 124 can determine the identity of part 122 by analyzing the outline of part 122 generated when the robotic part manipulator places the part in a predetermined position between a light source and an imaging component. In another embodiment, positioning system 124 can analyze a reflection image based on light emitted toward part 122 and reflected back to an imaging component. Radiation types other than light can be emitted. A detected image of part 122 can be analyzed by comparison to a standard image within a library of images accessible by positioning system 124. Comparison may include determining predetermined data points and comparing data points, overlaying images and determining differences, and other such methods known in the art.

In one embodiment, robotic part manipulation may include robotic positioning of part 122 with preset coordinates placing predetermined features of a part in a predetermined position relative to recognition equipment according to a positioning algorithm. Part manipulation can also include predetermined repositioning of a part during further steps of the inspection process. In a specific embodiment, robotic part manipulation can provide consistent part positioning during the inspection process which can reduce variation and can improve efficiency of the inspection process. In another embodiment, positioning system 124 can determine the positioning algorithm which would provide predetermined part manipulation based on part 122 identification.

Indication system 126 of inspection system 120 may include an image capture device such as but not limited to a camera which may be capable of capturing the visible spectrum, a photo-emission sensor for various wavelengths including but not limited to ultraviolet and x-ray, detectors capable of sensing electromagnetic radiation, and the like. Other capture devices structured to capture an indication from suitable indicators are also contemplated herein. A light source can be a laser, a discharge tube, or other radiation source. In a non-limiting exemplary embodiment, indication system 126 includes equipment with the capability to provide a radiation source to react with a fluorescent penetrant indicator causing an emission which can be detected by equipment of indication system 126. Equipment of indication system 126 can be contained in a single housing as shown in FIG. 1 or can be contained in separate housings. Indication system 126 can also include multiple radiation or illuminating sources and/or detection components. Components of indication system 126 can also provide illuminating and image acquisition for use with positioning system 124.

Controller 130 of surface inspection system 100 is shown in the embodiment of FIG. 1 as a single component containing hardware capable of performing various functions. Each function can be located on a separate piece of hardware and can be one of several hardware varieties available and arranged by one skilled in the art. Controller 130 can also include one or more microprocessors where, in one embodiment, a single microprocessor can provide the functions of each module or separate microprocessors can be used for one or more of the control modules. One skilled in the art would be able to determine a controller architecture.

Controller 130 in the embodiment of FIG. 1 is shown as being capable of operating an indication data processing system 132 and a robotic manipulation module 138. Indication data processing system 132 can include an analyzer module 134 with further details to follow and a sensor module 136. In one non-limiting form the analyzer module 134 is a fuzzy logic analyzer. In this embodiment, sensor module 136 can interact with indication system 126 to provide equipment controls as an alternative to controls provided directly with the indication equipment or from another source to interact with indication system 126. Sensor module 136 can be capable of providing acquisition and manipulation capabilities for data sets obtained by indication system 126.

In one embodiment, analyzer module 134 is a fuzzy logic analyzer module capable of providing analysis of the indication data sets from indication system 126. Fuzzy logic analysis provides a mathematical model of the vagueness found in non-precise measurements of surface inspection techniques such as but not limited to FPI and magnetic-particle inspection. Fuzzy logic can be used in machine control in order to deal with fuzzy concepts—concepts that cannot be expressed as "true" or "false" but rather as "partial truths."

Fuzzy logic analyzer module can include an input stage, a processing stage, a compilation stage and an output stage. The input stage maps sensor or other inputs to appropriate membership functions and truth values. The processing stage invokes an appropriate set of logic rules in the form of IF-THEN statements—IF variable IS property THEN action. The compilation stage combines the results of the rules. Finally, the output stage converts the combined results into a control output value.

For an automated surface inspection system, an indication data processing method in an embodiment of the present invention includes fuzzy logic analysis to enable a system to use an analysis tool with appropriate processing times for part inspection. In general, a fuzzy logic analysis system is a logic analysis system operable to process data by replacing what are commonly Boolean logic rules with a collection of fuzzy membership functions and rules. An example rule in a fuzzy logic system may be of the form:

If x is low and y is high, then z is low, where x and y are input variables, z is an output variable, "low" is a membership function defined on x and z, and "high" is a membership function defined on y.

Because fuzzy logic is a mathematical model for addressing inherently imprecise data, a fuzzy logic analysis can be applied to the present application. For an exemplary embodiment including a fluorescent penetrant indicator (FPI), surface anomalies are indicated by areas of brightness due to the presence of the fluorescent penetrant. The concept of 'brightness' is not mathematically expressed in an equation. Luminescence may be a quantity but 'brightness' is not. A sharp cut off does not exist between 'bright' and 'not bright.' One cannot simply say that 'bright' is at X luminescence but 'not bright' is at X−1 luminescence. During FPI for example, an operator may be able to infer differing 'brightness' for the areas of a sample with differing levels fluorescent penetrant responding to the radiation. How much 'brightness' recorded will vary between operators leading to reduced repeatability.

In an exemplary embodiment including FPI, a radiance data set is collected and compared to a set of rules assigning a degree of intensity to the radiance data set. The degree of intensity in this embodiment is a representation of the amount of radiance the fluorescent penetrant produces when radiated. The degree of intensity may be representative of other levels of indicators in other embodiments. Continuing with this embodiment, the degree of intensity is compiled to produce an output data set related to position and level of radiance. The output data set is compared to data sets in a knowledge bank to determine whether the output data sets are consistent with anomalies. Output data sets consistent with anomalies provide an indication of the anomalies present in the component.

Automated review of the radiance data set in this embodiment is capable of reducing variation found in surface variance detection.

Robotic manipulation module 138 is shown in FIG. 1 as part of controller 130. Robotic manipulation module 138 can, in the alternative, be part of the positioning equipment in positioning system 124 as a single system or as separate components. For one embodiment, robotic manipulation module 138 is capable of providing a positioning algorithm, a component type recognition database and predetermined part manipulation instructions.

A positioning algorithm can include predetermined coordinates for a robotic part manipulator where coordinates can be based on an absolute or comparative capacity. For one embodiment, once a part has been identified and the position of certain features determined in relation to a part manipulator, a positioning algorithm produces predetermined rotation and positioning of the part during inspection thereby increasing the consistency in detecting variances with recognition equipment. For example, in one embodiment, inspection begins with predetermined initial coordinates within the robotic manipulator's coordinate measuring system. The positioning algorithm could then control movement of the part manipulator allowing the inspection to be systematically applied to related components.

Surface inspection system 100 of FIG. 1 can also include a final cleaning process 140 which may allow a part 122 to be returned to a manufacturing line following a surface inspection test. The care and degree of cleaning necessary can depend on the remaining manufacturing processes and the final function of the parts being tested.

Features of a surface indicated by an embodiment of surface inspection system 100 can include but are not limited to micro and macro porosity, inclusion defects, inhomogeneities, and discontinuities. In some embodiments the part would include a single crystal, a directionally solidified, and/or an equiaxed microstructure. In a further embodiment the part could include an airfoil component of a gas turbine engine. Another embodiment can operate to mechanically locate, evaluate, and report surface variances on families of airfoil type components. Yet another embodiment of the present application generates a report of the sizes and locations of the variances on the surface of a component in tabular or graphical form.

Figure 2:
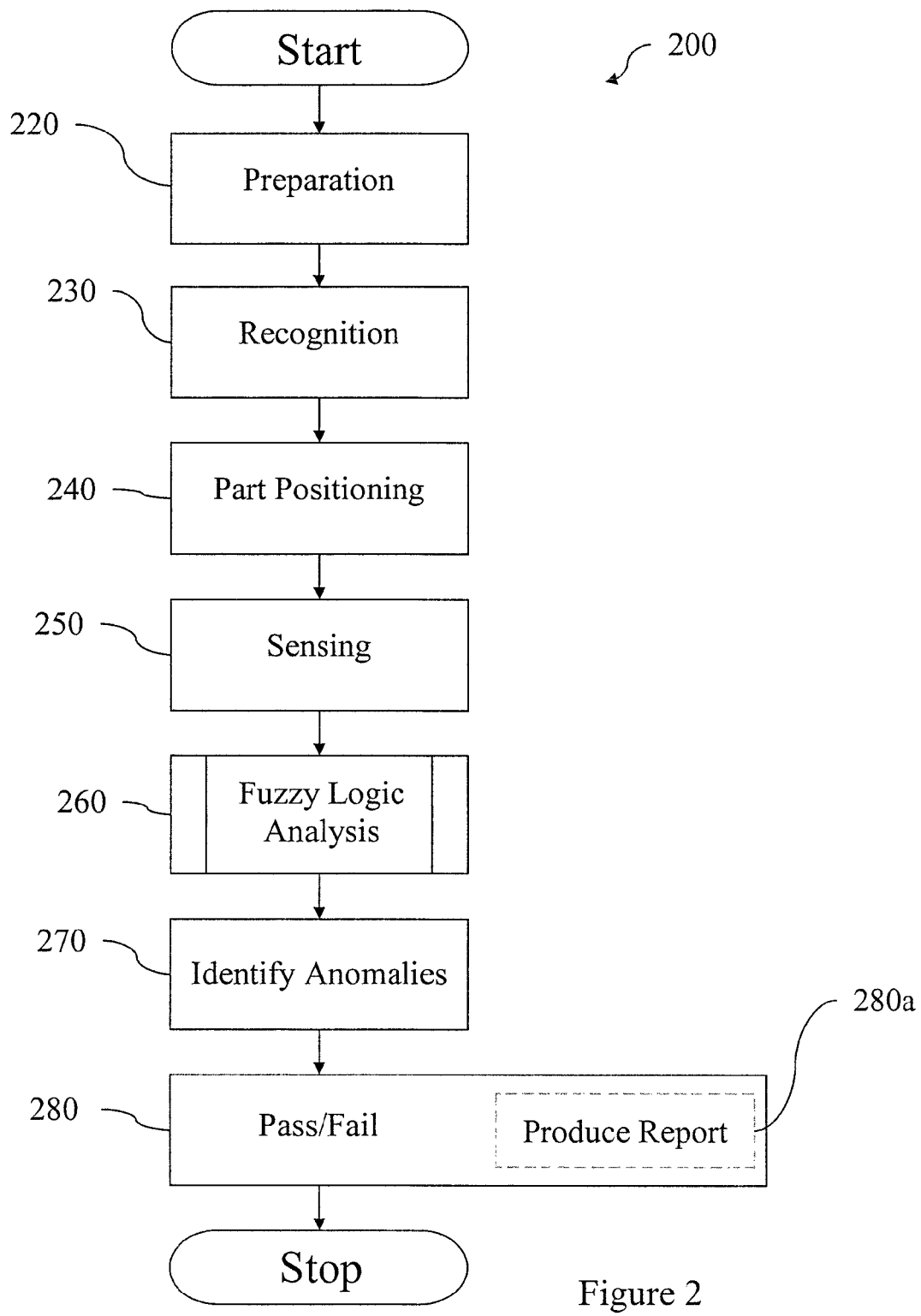
FIG. 2 is a flow diagram of one embodiment of an inspection process.

With regards to FIG. 2, an exemplary inspection process 200 is shown. Inspection process 200 begins with operation 220 which includes surface defect indicator preparation. Shown as following operation 220 in process 200 is optional operation 230 which includes recognizing the part being tested. The recognition in operation 230 can be based on a comparison with the sensed image of the part and a database of part responses. Operation 240 is then capable of applying a predetermined positioning algorithm based on the automated recognition of operation 230 to manipulate the part. Automatic part positioning may reduce variability and improve the efficiency of the test.

As the part is manipulated with operation 240, operation 250 provides a source of excitement and senses the response from the surface of the part to collect an indication data set. In one embodiment, UV radiation is directed toward a surface of a test part to irradiate a fluorescent dye. In another embodiment, ferrous iron particles are placed on a ferromagnetic component's surface and a magnetic field is applied to the component. The magnetic flux of the applied magnetic field leaks at surface anomalies. The iron particles are attracted to areas of flux leakage producing an indicator of the surface anomalies.

Figure 3:
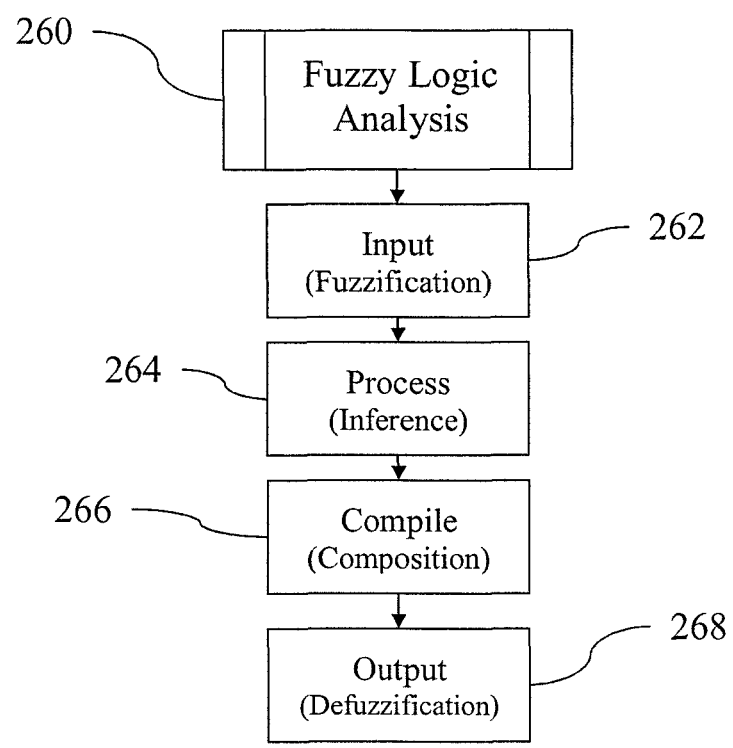
FIG. 3 is a flow diagram of a process from FIG. 2.

The indication data collected during operation 250 is provided to operation 260 which applies a fuzzy logic analysis. FIG. 3 shows further detail regarding operation 260 where, in one embodiment, four exemplary operations are part of a fuzzy logic analysis. These operations may be described in slightly differing terms and may be combined, expanded or omitted based on the way the fuzzy logic analysis is described without changing the meaning or intent of using fuzzy logic in this embodiment of the present invention.

1. Input Stage—Fuzzification (262): The membership functions defined for the input variables can be applied to the actual values of the input variables to determine the degree of truth for each rule premise. The input variables in a fuzzy control system can be, in general, mapped into sets of membership functions known as "fuzzy sets" in the process of converting an input value to a fuzzy value. Any of the rules that apply can be invoked, using the membership functions and truth values obtained from the inputs, to determine the results of the rules.
2. Processing stage—Inference (264): The truth value for the premise of each rule may be computed and applied to its consequent. This computation results in one fuzzy subset being assigned to each output variable. The computation result may be mapped into a membership function and truth value controlling the output variable.
3. Compilation stage—Composition (266): All of the fuzzy subsets assigned to each output variable may be combined together to form a single fuzzy output subset for each output variable.
4. Output stage—Defuzzification (268): The fuzzy output subset for each output variable may be convertible to a unique solution or a 'crisp' answer.

Returning to FIG. 2, Operation 270 follows the fuzzy logic analysis in operation 260. Operation 270 allows an automated identification of anomalies on the surface of the part as indicated by the indicator. The anomalies can be inhomogeneities, microstructural discontinuities, inclusions, micro-porosity, grain structure and combinations thereof. The fuzzy logic algorithm from operation 260 can produce a characterization data set for comparison with a knowledge bank. This comparison in Operation 270 allows the automated inspection process to apply cognitive characterization of defects indicated by an indication process. In one embodiment, the knowledge bank includes, but is not limited to, data sets from previous surface inspection applications to standard components or data sets generated from theoretical calculations or simulations. Fuzzy logic analysis and cognitive characterization in operation 270 can directly affect the ability to determine an automated pass/fail status for the part.

Operation 280 includes the application of an accept/reject criteria which utilizes the results from the fuzzy logic algorithm in operation 260 and the anomaly indication in operation 270. Operation 280 can also provide a report (280a) regarding the anomalies from operation 270 and the results of the fuzzy logic analysis in operation 260. For some embodiments, the report from operation 280 can be in tabular or graphical form intended to communicate the location and degree of deviation for the indicated anomalies.

Using one embodiment of the present invention, inspection process variation can be greatly reduced via automating the detection of variances and the application of a pass/fail criteria using fuzzy logic analysis. Fuzzy logic analysis allows an automated inspection to access a knowledge bank to apply cognitive characterization of defects and provide a level of consistency to determine a pass/fail status according to a specification.

Another embodiment of the present application applies a special lighting configuration, a part presentation technique, and a fuzzy logic based image processing technique for identifying inhomogeneity in a single crystal cast airfoil component using a fluorescent penetrant process. Yet another embodiment includes an algorithm for manipulating a part with respect to lighting and camera positions in an efficient manner with minimum hunting and a fuzzy logic based image processing algorithm to identify anomalies which may indicate a surface defect. Embodiments from the present application can be applied to components utilizing FPI or magnetic-particle defect inspection such as but not limited to single crystal cast components, directionally solidified cast components, and equiax solidified cast components.

One aspect of the present application is an apparatus including a positioning system; a surface indicator system structured to collect an indication data set from a surface of a component; an indication data processing system structured to create an output data set in response to the indication data set utilizing a fuzzy logic algorithm; and a microprocessor structured to provide at least one surface variance in response to the indication data set and the output data set.

A feature of this aspect includes the positioning system further having a manipulator structured to position the component in response to a positioning algorithm and the positioning algorithm identifying the component with a component position database in response to the indication data set and a recognition source data set. Another feature includes the surface indicator system having an indication device capable of collecting the indication data set and the indication device having an indicator application system capable of applying an indicator material to the surface of the component. Further features can include the at least one surface variance having a variance selected from a group consisting of inhomogeneities, microstructural discontinuities, inclusions, micro and macro porosity and combinations thereof; a pass/fail signal; and a variance report.

Another aspect of the present application is a method including conducting a surface indication technique for a component; utilizing a positioning algorithm to manipulate at least one piece of positioning equipment in response to the component; directing an indication source to a surface of the component; collecting an indication data set in response to directing the indication source to the surface of the component; applying a fuzzy logic analysis in response to the indication data set capable of providing an output data set; and providing at least one surface variance in response to the output data set.

Features of this aspect can include the surface indication technique being fluorescent penetration process; and the fuzzy logic analysis having an input collecting module, a processing module, a compiling module, and an output collecting module where the input collecting module further includes collecting the indication data set and the output collecting module further includes collecting the output data set.

Further features include performing a part recognition method with a component position database in response to at least one of the indication data set, a light source data set, and a recognition source data set; and the at least one piece of positioning equipment having a robotic manipulator structured to position the component in response to the component and the positioning algorithm. Still further features can include the at least one surface variance having a variance selected from a group consisting of inhomogeneities, microstructural discontinuities, inclusions, micro-porosity, and combinations thereof; a pass/fail signal; and a variance report.

Yet another aspect of the present application is an apparatus including a positioning system having a manipulator device structured to position a component in response to a positioning algorithm; an indication system structured to collect an indication data set utilizing a fluorescent penetration process; an indication data processing system utilizing a fuzzy logic algorithm capable of: applying the indication data set as a set of input variables; assigning a degree of intensity to the set of input variables; determining an output data set; and converting the output data set to a set of solutions; and a microprocessor structured to provide at least one surface variance in response to the set of solutions. A feature of this aspect can include providing the at least one surface variance further includes characterization of at least one surface anomaly.

Still another aspect of the present application provides an apparatus comprising a positioning system, a surface indicator system structured to collect an indication data set from a surface of a component, a surface indicator composition applied to the component and configured to emit an indication that can be sensed by the surface indication system, an indication data processing system structured to create an output data set in response to the indication data set utilizing a fuzzy logic algorithm, and a microprocessor structured to provide at least one surface variance in response to the indication data set and the output data set.

Features of the present application include: wherein the positioning system further includes a manipulator structured to position the component in response to a positioning algorithm, and wherein the surface indicator composition can emit an electromagnetic signal; wherein the positioning algorithm further includes identifying the component with a component position database in response to the indication data set and a recognition source data set; wherein the surface indicator composition is a Fluorescent Penetrant Indicator (FPI); wherein the indication device further includes an indicator application system capable of applying the FPI to the surface of the component; wherein the at least one surface variance includes a variance selected from a group consisting of inhomogeneities, microstructural discontinuities, inclusions, micro and macro porosity and combinations thereof; wherein the at least one surface variance further includes a pass/fail signal; and wherein the at least one surface variance further includes a variance report.

Still another aspect of the present application provides a method comprising applying a surface indicator material to a component, utilizing a positioning algorithm to manipulate at least one piece of positioning equipment in response to the component, directing an indication source to a surface of the component having the surface indicator material, collecting an indication data set in response to directing the indication source to the surface of the component, applying a fuzzy logic analysis in response to the indication data set, the fuzzy logic analysis capable of providing an output data set, and providing at least one surface variance in response to the output data set.

Features of the present application include wherein the surface indicator material is configured for use in a fluorescent penetration process, wherein the fuzzy logic analysis includes an input collecting module, a processing module, a compiling module, and an output collecting module; wherein the input collecting module further includes collecting the indication data set; wherein the output collecting module further includes collecting the output data set. Features also further include performing a part recognition method with a component position database in response to at least one of the indication data set, a light source data set, and a recognition source data set. Further features provide wherein the at least one piece of positioning equipment further includes a robotic manipulator structured to position the component in response to the component and the positioning algorithm; wherein the at least one surface variance includes a variance selected from a group consisting of inhomogeneities, microstructural discontinuities, inclusions, micro-porosity, and combinations thereof; wherein the at least one surface variance further includes a pass/fail signal; wherein the at least one surface variance further includes a variance report.

Yet still further aspects of the present application provide an apparatus comprising a positioning system having a manipulator device structured to position a component in response to a positioning algorithm, an indication system structured to collect an indication data set utilizing a fluorescent penetration process, an indication data processing system utilizing a fuzzy logic algorithm capable of: applying the indication data set as a set of input variables, assigning a degree of intensity to the set of input variables, determining an output data set, and converting the output data set to a set of solutions, and a microprocessor structured to provide at least one surface variance in response to the set of solutions.

A feature of the present application provides wherein providing the at least one surface variance further includes characterization of at least one surface anomaly.

While the invention has been illustrated and described in detail in the drawings and foregoing description, the same is to be considered as illustrative and not restrictive in character, it being understood that only the preferred embodiments have been shown and described and that all changes and modifications that come within the spirit of the inventions are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. An apparatus comprising:
   a positioning system;
   a surface indicator system structured to collect an indication data set from a surface of a component;
   a surface indicator composition applied to the component and configured to emit an indication that can be sensed by the surface indication system;
   an indication data processing system structured to create an output data set in response to the indication data set utilizing a fuzzy logic algorithm; and
   a microprocessor structured to provide at least one surface variance in response to the indication data set and the output data set.

2. The apparatus of claim 1, wherein the positioning system further includes a manipulator structured to position the component in response to a positioning algorithm, and wherein the surface indicator composition can emit an electromagnetic signal.

3. The apparatus of claim 2, wherein the positioning algorithm further includes identifying the component with a component position database in response to the indication data set and a recognition source data set.

4. The apparatus of claim 1, wherein the surface indicator composition is a Fluorescent Penetrant Indicator (FPI).

5. The apparatus of claim 4, wherein the indication device further includes an indicator application system capable of applying the FPI to the surface of the component.

6. The apparatus of claim 1, wherein the at least one surface variance includes a variance selected from a group consisting of inhomogeneities, microstructural discontinuities, inclusions, micro and macro porosity and combinations thereof.

7. The apparatus of claim 6, wherein the at least one surface variance further includes a pass/fail signal.

8. The apparatus of claim 6, wherein the at least one surface variance further includes a variance report.

9. A method comprising:
   applying a surface indicator material to a component;
   utilizing a positioning algorithm to manipulate at least one piece of positioning equipment in response to the component;
   directing an indication source to a surface of the component having the surface indicator material;
   collecting an indication data set in response to directing the indication source to the surface of the component;
   applying a fuzzy logic analysis in response to the indication data set, the fuzzy logic analysis capable of providing an output data set; and
   providing at least one surface variance in response to the output data set.

10. The method of claim 9, wherein the surface indicator material is configured for use in a fluorescent penetration process.

11. The method of claim 9, wherein the fuzzy logic analysis includes an input collecting module, a processing module, a compiling module, and an output collecting module.

12. The method of claim 11, wherein the input collecting module further includes collecting the indication data set.

13. The method of claim 11, wherein the output collecting module further includes collecting the output data set.

14. The method of claim 9, further including performing a part recognition method with a component position database in response to at least one of the indication data set, a light source data set, and a recognition source data set.

15. The method of claim 9, wherein the at least one piece of positioning equipment further includes a robotic manipulator structured to position the component in response to the component and the positioning algorithm.

16. The method of claim 9, wherein the at least one surface variance includes a variance selected from a group consisting of inhomogeneities, microstructural discontinuities, inclusions, micro-porosity, and combinations thereof.

17. The method of claim 16, wherein the at least one surface variance further includes a pass/fail signal.

18. The method of claim 16, wherein the at least one surface variance further includes a variance report.

19. An apparatus comprising:
    a positioning system having a manipulator device structured to position a component in response to a positioning algorithm;
    an indication system structured to collect an indication data set utilizing a fluorescent penetration process;
    an indication data processing system utilizing a fuzzy logic algorithm capable of:
    applying the indication data set as a set of input variables;

assigning a degree of intensity to the set of input variables;
determining an output data set; and
converting the output data set to a set of solutions; and
a microprocessor structured to provide at least one surface variance in response to the set of solutions.

20. The apparatus of claim 19, wherein providing the at least one surface variance further includes characterization of at least one surface anomaly.

* * * * *